United States Patent [19]
Zachariades

[11] Patent Number: 5,030,402
[45] Date of Patent: Jul. 9, 1991

[54] PROCESS FOR PRODUCING A NEW CLASS OF ULTRA-HIGH-MOLECULAR-WEIGHT POLYETHYLENE ORTHOPAEDIC PROSTHESES WITH ENHANCED MECHANICAL PROPERTIES

[76] Inventor: Anagnostis E. Zachariades, 65 Glengarry Way, Hillsborough, Calif. 94010

[21] Appl. No.: 325,563

[22] Filed: Mar. 17, 1989

[51] Int. Cl.$^5$ ....................... B29C 43/04; B29C 43/36
[52] U.S. Cl. .................................... 264/138; 264/163; 264/322; 264/323
[58] Field of Search .................. 264/322, 323, 331.17, 264/138, 163

[56] References Cited

U.S. PATENT DOCUMENTS

| | | | |
|---|---|---|---|
| 2,232,475 | 2/1941 | Renfrew et al. | 264/331.17 |
| 3,079,642 | 3/1963 | Needham et al. | 264/320 |
| 3,733,159 | 5/1973 | Coffman | 264/320 |
| 3,944,536 | 3/1976 | Lupton et al. | 264/331.17 |
| 4,014,970 | 3/1977 | Jahnle | 264/322 |
| 4,587,163 | 5/1986 | Zachariades | 264/322 |
| 4,747,990 | 5/1988 | Ganssens et al. | 264/331.17 |
| 4,874,657 | 10/1989 | Lo et al. | 264/323 |

Primary Examiner—James Lowe
Attorney, Agent, or Firm—Owen, Wickersham & Erickson

[57] ABSTRACT

A method for producing an UHMWPE product with enhanced planar mechanical properties. An initial UHMWPE semicrystalline morphology is solid-state deformed under compression in a mold including a mold cavity with an unenclosed perimeter zone or a perimeter zone with a reservoir enabling flow-through for molded UHMWPE. A polymer preform is oriented and extended in more than one direction in the mold cavity and the perimeter zone to an extent which is limited by the material properties of the polymer under the employed processing conditions. The oriented and extended UHMWPE is cooled under compression to ambient temperature for maintaining the maximum orientation and extension attained during the solid-state deformation process. The polymer product in the mold cavity is separated from the product in the perimeter zone of the mold cavity. The UHMWPE product has a markedly transformed morphology, as compared with the initial UHMWPE morphology. The product comprises oriented and extended molecular chains in more than one direction and exhibits markedly enhanced mechanical properties in more than one direction, the magnitude depending on the extent of deformation.

18 Claims, 6 Drawing Sheets

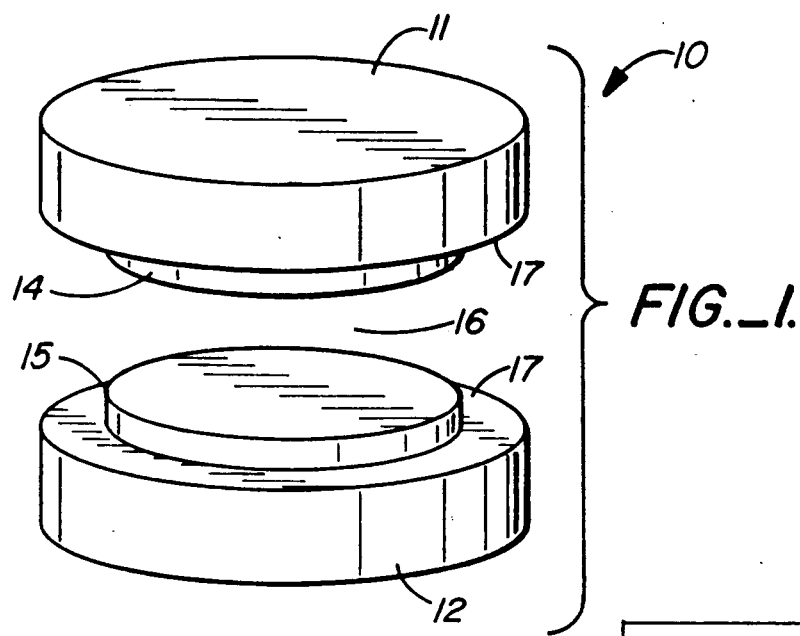
FIG._1.
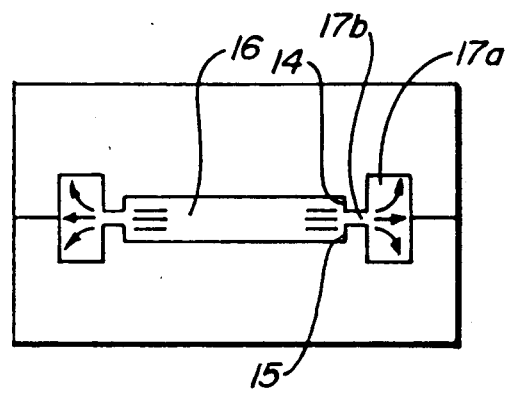
FIG._II.
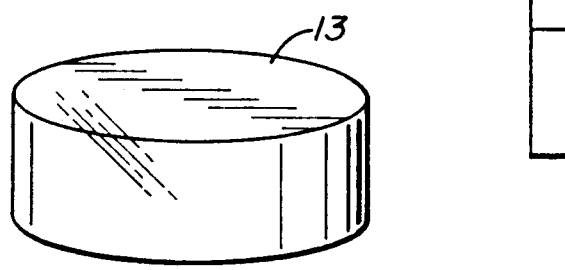
FIG._1A.
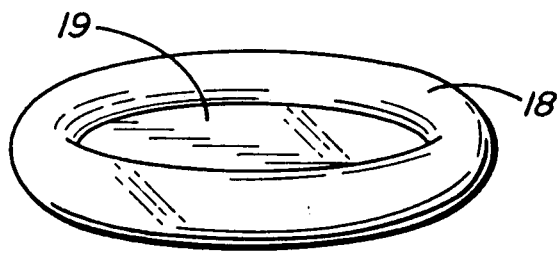
FIG._1B.
FIG._1C.

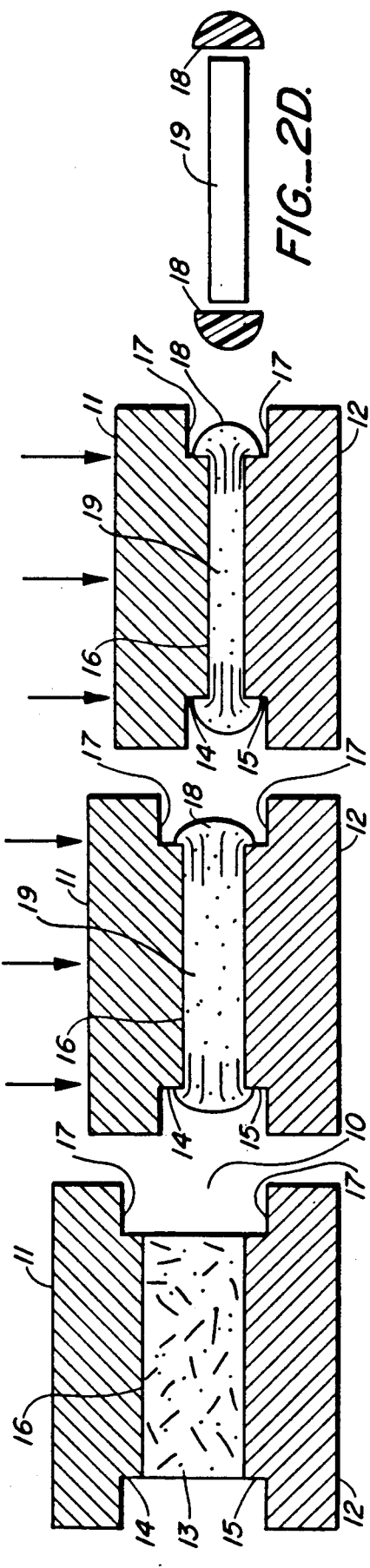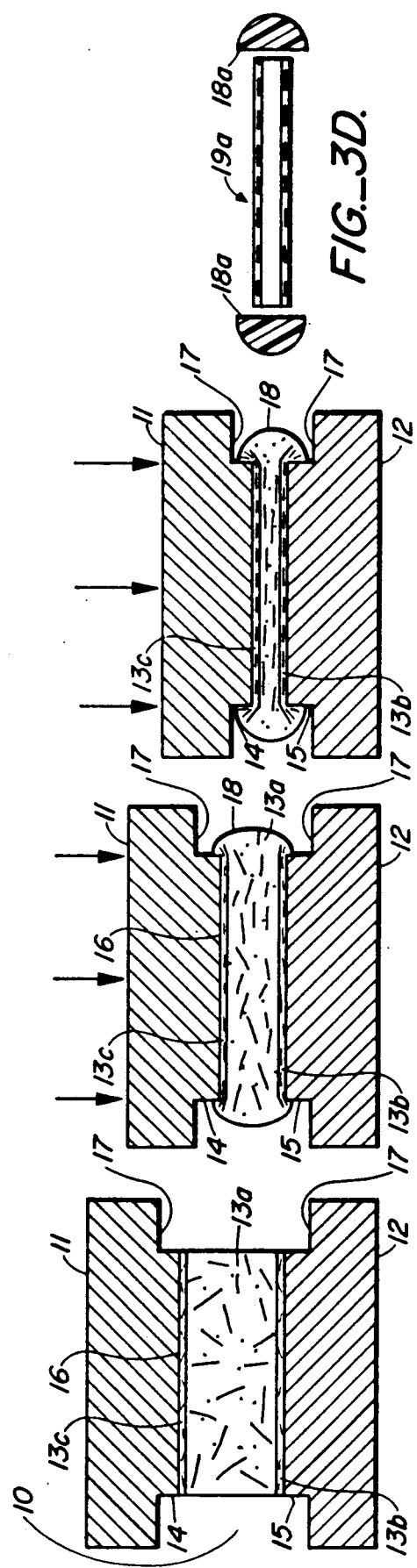

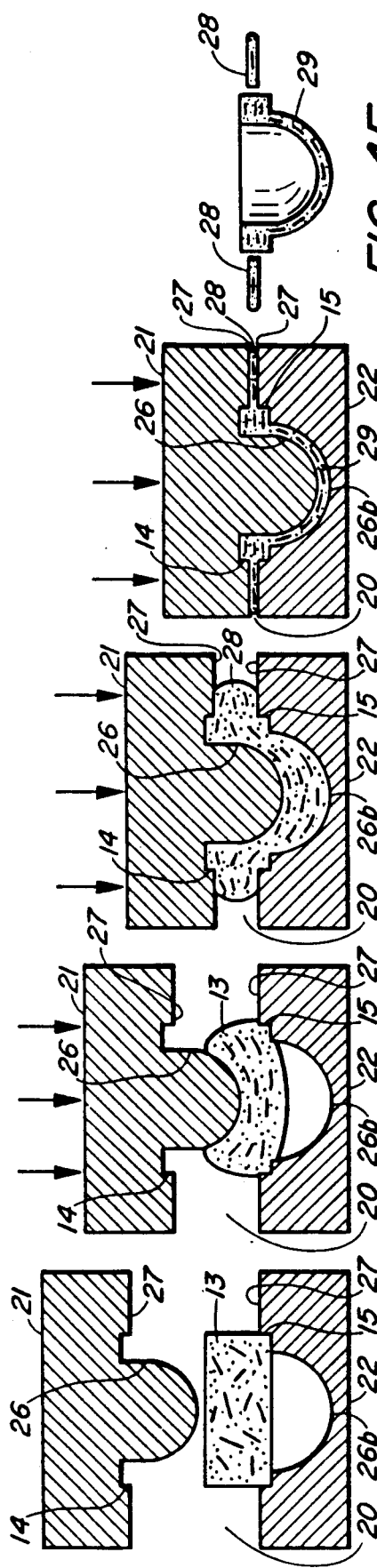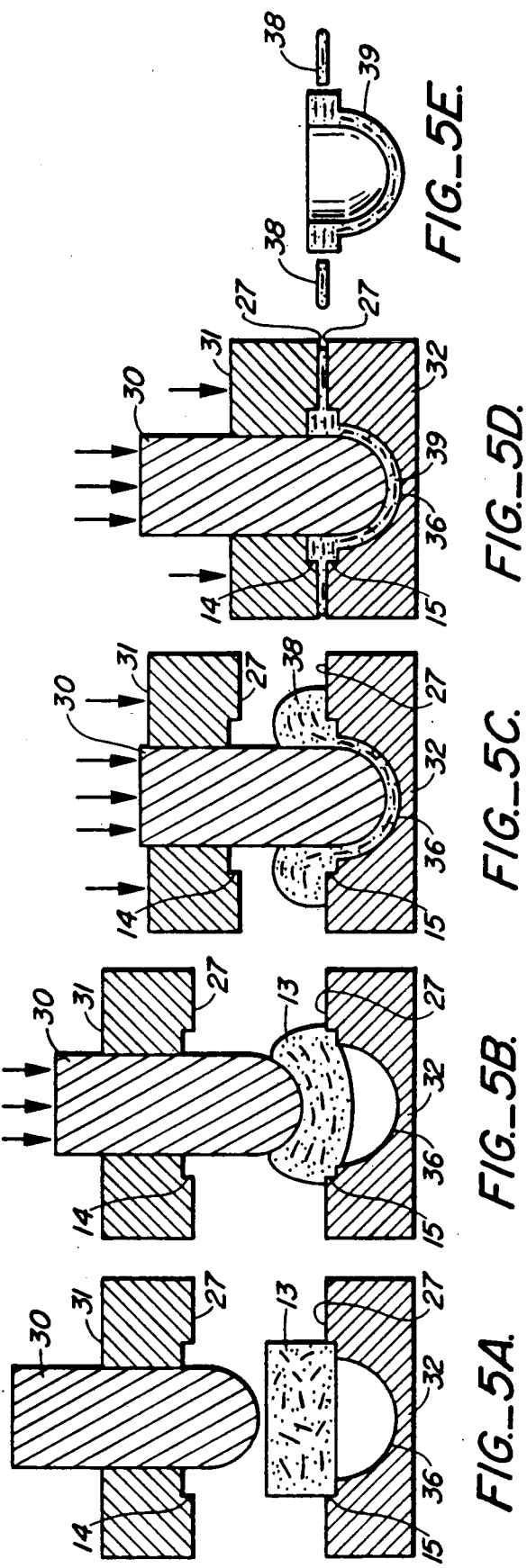

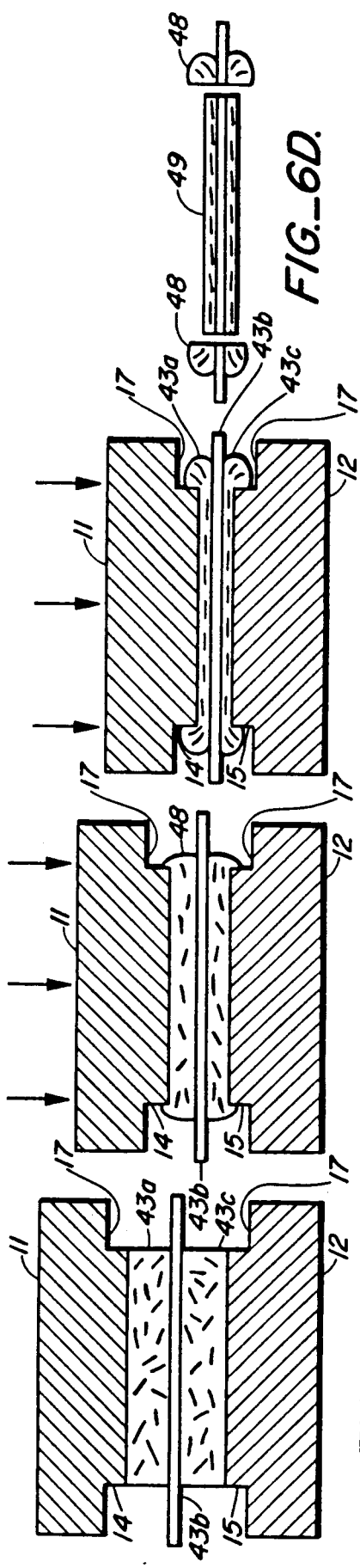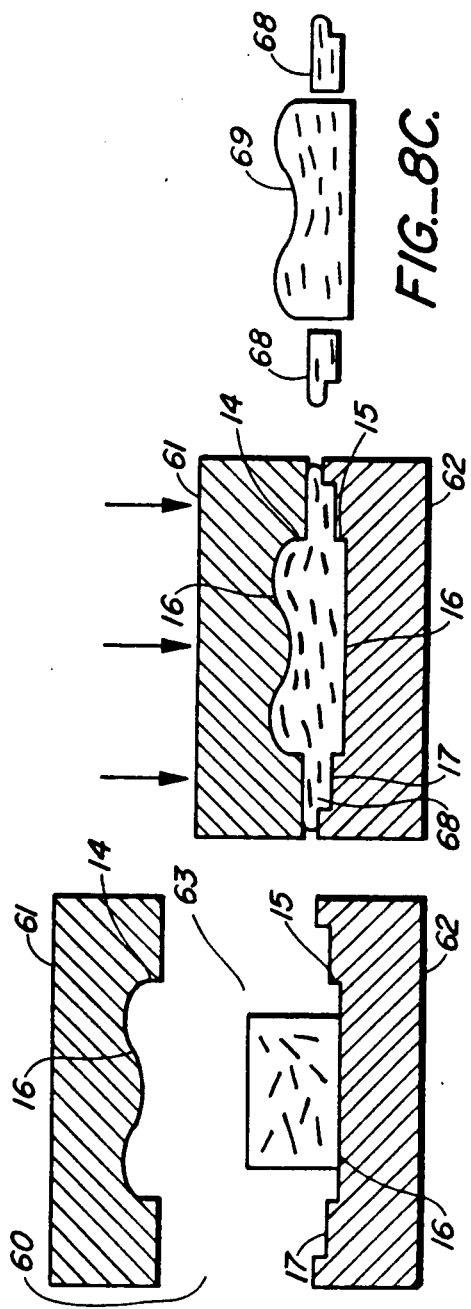

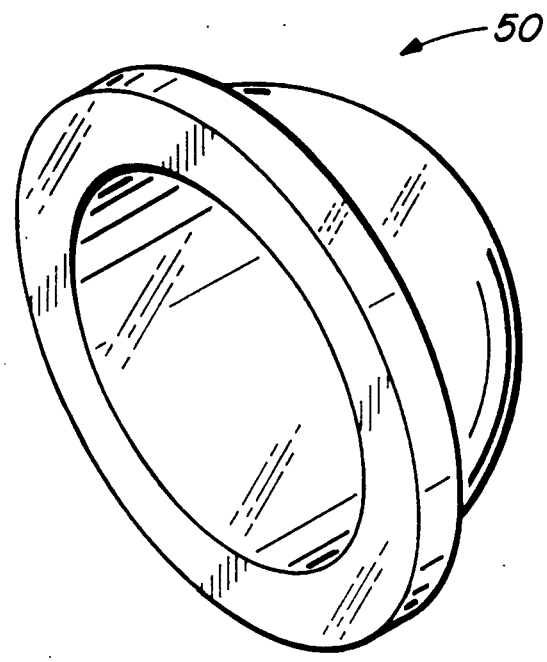
FIG._7.
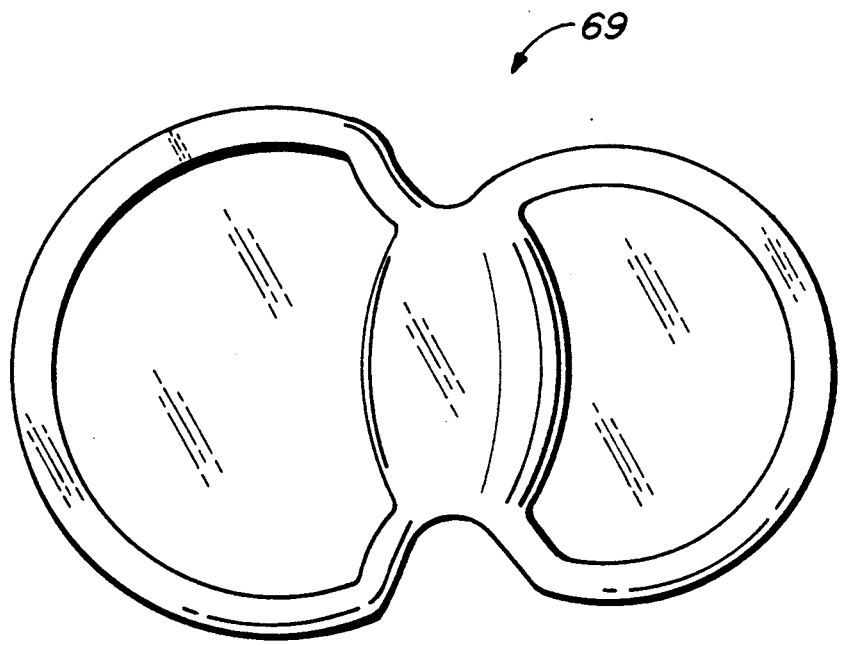
FIG._9.

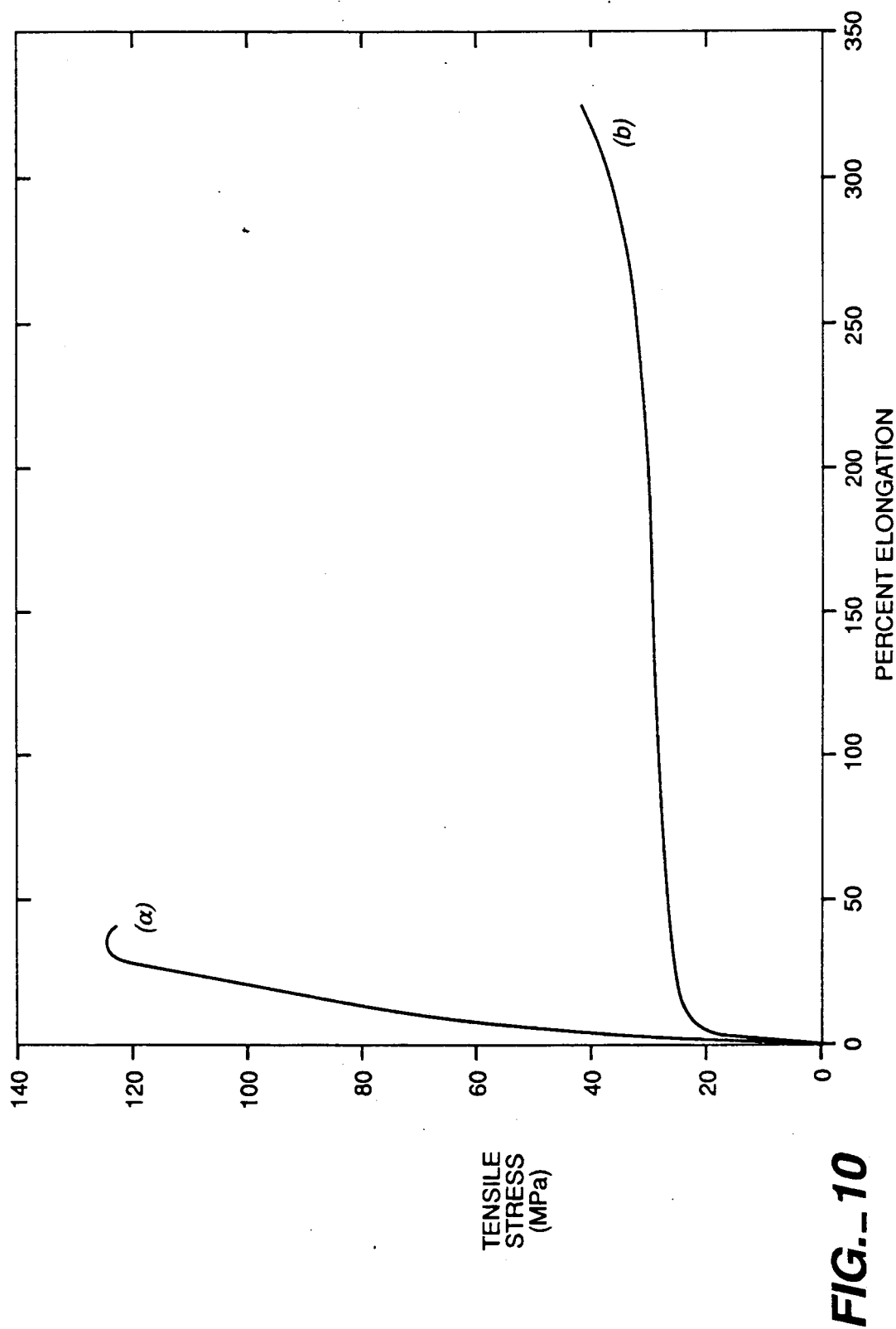
FIG._10

PROCESS FOR PRODUCING A NEW CLASS OF ULTRA-HIGH-MOLECULAR-WEIGHT POLYETHYLENE ORTHOPAEDIC PROSTHESES WITH ENHANCED MECHANICAL PROPERTIES

FIELD OF THE INVENTION

This invention relates to a novel solid-state-deformation process for producing ultra-high-molecular-weight polyethylene products of both simple and complex shapes, with enhanced mechanical properties. It also relates to the resultant product.

BACKGROUND OF THE INVENTION

The art of controlling the magnitude and the directionality of the physical and mechanical properties of polymers has been a subject of considerable interest to polymer engineers in recent years. Whereas the magnitude has been the basic objective of numerous molecular deformation processes by which the tensile properties can be enhanced significantly, as a result of the chain orientation and extension in some particular direction, usually the machine direction, the directionality has been traditionally addressed by the construction of fiber-reinforced composite structures. In conventional meltprocessing, where the objective is the conversion of a polymer raw material into a solid product of some specific shape, the traditional approaches of controlling the thermomechanical history of the polymer melt have not been efficient enough for controlling the properties of the final product. The reason is that some of the chain orientation and extension obtained (produced in the feeding and/or processing zones) has tended to relax through an uncontrolled molecular relaxation process before the polymer has been completely solidified in the forming and/or shaping stage. The basic objective of obtaining a product of some specified shape has been met, but such a product has had non-isotropic properties.

Homogeneous polymer structures (i.e., structures without fillers or fiber reinforcement) with enhanced mechanical properties in planar directions have been produced recently This has been done by induced crystallization under curvilinear flow conditions and by solid-state-forming processes. This has resulted in products with multiaxial chain orientation and extension and products with an overall biaxial (but unbalanced) chain orientation and extension. The first approach is more suitable for processing readily melt-processable polymers by rapid output processes, whereas the latter approach can be used also for processing more intractable polymers, such as ultra-high-molecular-weight polyethylene.

For example, a solid-state-forming process of Dow Chemical (known as the SPF Process), is a process for the development of containers with biaxial orientation; the SPF Process comprises the forging of a lubricated polymer preform or a briquette, at a temperature between the softening point and the melt point of the polymer, into a sheet preform, which is automatically clamped and cooled at its periphery and then plug-assist and pressure-formed into a cooled mold to the shape of the finished article (the container). Although the overall orientation of the product is biaxial and results in the substantial enhancement of its mechanical properties, the way it is generated is unbalanced and cannot be controlled to vary topologically in a non-symmetrical fashion (i.e., unlike the deep-draw process).

Similarly, the solid-state-forming process disclosed in U.S. Pat. No. 4,747,990 involves the shaping of a polyethylene resin in a closed-mold configuration; the deformation of the polymer (and hence the degree of chain orientation) is non-uniform in different parts of the product, e.g., of the material close to and against the plunger versus the material against the lower part of the mold cavity.

Both the SPF Process and the process disclosed in U.S. Pat. No. 4,747,990, as well as other solid-state-forming processes, e.g., the matched mold forging process, operate under "closed mold" conditions. In the SPF Process the outer clamping ring on the periphery of the mold provides a physical constraint to the maximum deformation that one can deform the polymer under compression during the forging step for the fabrication of the sheet preform. Similarly, in the other processes, e.g., the process of U.S. Pat. No. 4,747,990, the maximum deformation is controlled by the ratio of the polymer preform dimensions to the mold dimensions.

In addition, many applications may benefit from the development of products with enhanced planar mechanical properties and these require good dimensional stability.

In the case of ultra-high-molecular-weight polyethylene it is very difficult to control this important parameter: first, because this polymer is dimensionally unstable, even during a simple machining operation; second, because when this polymer is oriented, it exhibits a remarkable springback, which also affects the magnitude of the properties of the final product. (Springback refers to the tendency of a formed product to revert partially to its original configuration after removing a compression or tension load, and it is a major concern in solid-state-forming operations.)

Thus, the fabrication of ultra-high-molecular-weight polyethylene products to achieve enhanced mechanical properties and good dimensional stability is a challenging task. Also, it is important to realize that polymer structures with enhanced planar mechanical properties can be used at substantially reduced thicknesses, thus reducing the unnecessary bulk of material that is currently used in many applications for increasing their load-bearing performance. For example, in the case of orthopaedic prosthetic products, e.g., acetabular liner and tibial plates, their thickness can be reduced without sacrificing their mechanical performance.

An object of this invention is the fabrication of a molded ultra-high-molecular-weight polyethylene product with enhanced and balanced planar mechanical properties and controlled dimensional stability.

Another object of this invention is the fabrication of such an ultra-high-molecular-weight polyethylene product by using an "open mold" configuration.

Another object of this invention is the compression molding of an ultra-high-molecular-weight polyethylene to a deformation ratio which is unrelated to the ratio of the physical dimensions of the polymer preform and the mold cavity and, in contrast, depends only on the material properties of the polymer under the employed processing conditions.

A further object of this invention is the fabrication of wear-bearing ultra-high-molecular-weight polyethylene products of thinner load, having enhanced mechanical properties.

SUMMARY OF THE INVENTION

This invention produces ultra-high-molecular-weight polyethylene products with enhanced and balanced planar mechanical properties. It includes the product and a method of making such products for applications benefiting from their enhanced mechanical properties and abrasion performance with enhanced load and/or wear bearing capacity.

Under the scope of this invention, the term "ultra-high-molecular-weight polyethylene" (UHMWPE), means those polyethylenes which have been defined by ASTM 4020-81 as those linear polyethylenes which have a relative viscosity of 2.3 or greater at a solution concentration of 0.05% in decahydronapthalene. This definition applies alike to the description that follows and to the claims.

The nominal weight average molecular weight of the so-defined UHMWPE is several million; it is greater than three million and usually from three to six million; however, other linear polyethylenes of weight-average molecular weight greater than 500,000 and preferably above one million are included within the definition first given.

The present invention provides for the preparation of an UHMWPE product with balanced chain orientation and extension and hence superior mechanical properties. The product is made by compression molding UHMWPE in the form of a preformed solid blank heated at between 80° C. and the melting temperature of the polymer used, e.g., approximately 140° C. for the as-received powder stock, and preferably between 100° C. and 130° C., using a non-enclosed mold design which is heated in the range of 120° C. and 180° C., especially between 120° C and 165° C in which the UHMWPE preform can be biaxially deformed under extensional or shear flow conditions. The product is preferably deformed to a deformation ratio which strictly depends on the material properties of the UHMWPE at the processing conditions rather than the geometrical boundaries of an enclosed mold cavity rather than the geometrical boundaries of an enclosed mold cavity. The product is simultaneously shaped into the final product.

Because a so-produced UHMWPE has enhanced mechanical properties, the final product can be designed to have a reduced thickness dimension, as compared to UHMWPE produced currently by conventional molding or machining.

The processing methodology of the present invention comprises the solid-state deformation of the UHMWPE preform of a cylindrical or other suitable shape and having a volume greater than the mold cavity formed by a pair of molding plates by compressing it between the two molding plates (incorporating the actual mold cavity with the practically moldable design or geometrical details) to produce the shape of the final product, and a perimeter access zone for allowing the excess of polymer in the mold cavity to deform past the mold cavity during its compression between the mold plates for the purpose of controlling the extent of the deformation of the polymer in the mold cavity. The extent of deformation in the polymer can be determined from the thickness reduction ratio of the polymer preform to its deformation to the final product, or alternatively by the displacement of fiducial marks on the surface of the preform. The polymer deforms in the solid-state past the mold cavity to the mold plate boundaries or beyond.

By deforming the polymer past the actual mold cavity a) the extent of the molecular chain extension and orientation can be controlled throughout in the final product, an important objective of this invention and b) the excess polymer which deforms past the mold cavity acts as an in-situ-generating tenter frame which can hold the compression deformed polymer in the mold cavity under tension when the compression load is removed after cooling the mold to ambient temperature and hence aid in retaining the attained chain orientation and extension past the compression operation. The so-compression-deformed product in the mold cavity can be maintained attached with the deformed polymer in the perimeter zone for sufficient time after processing until the polymer relaxes in its deformed state or for post-processing such as cross-linking radiation under tension; alternatively; it can be cut off by stamping or other process.

Unlike the conventional compression molding process or the solid-state-forming processes of the prior art, the process of this application requires the employment of high pressure of greater than 20 MPa and preferably above 50 MPa for a) controlling the uniformity of the chain orientation and extension in the product and b) for undercooling the polymer preform when the mold temperature is maintained above the melting temperature of the polymer.

This processing approach is versatile. It makes possible 1) the fabrication of products with enhanced mechanical properties and having practically any planar shape, 2) the fabrication of products with planar or three-dimensional chain orientation and extension, 3) the fabrication of products with enhanced planar mechanical properties by solid-state deforming to a deformation ratio which depends only on the material properties of the polymer, rather than the physical constraints of the mold cavity, 4) the fabrication of products with mechanical properties which can be designed to be topologically different. This can be accomplished by the use of a polymer preform with larger dimensions and geometrical configuration different from the mold plates.

5) the fabrication of composite products with enhanced planar mechanical properties comprised of the same or different polymer resins, 6) the fabrication of fiber-reinforced composite products comprised of a biaxially solid-state deformed matrix of UHMWPE or other suitable polymer resin and UHMWPE or other suitable reinforcing fibers e.g., aramid, glass, and carbon fibers.

BRIEF DESCRIPTION OF THE DRAWINGS

FIG. 1 is a schematic representation in perspective of an opened mold embodying the principles of the present invention with a polymer preform shown between the mold plates.

FIG. 1A is a perspective schematic representation of a mold preform before it is placed between the two mold halves and the mold closed.

FIG. 1B is a perspective view of the molded product removed from the mold.

FIG. 1C is a similar view of the product which results from trimming the perimeter polymer compressed from the product of FIG. 1B.

FIG. 2 is a schematic diagram similar to FIG. 1, of a polymer preform, both outside the mold and between a pair of mold plates (FIG. 2A) as it is being deformed (FIG. 2B and 2C) into a final disc-like product (FIG. 2D), and it shows a plurality of different stages of the process. Three stages, A, B, and C are shown. The lines in the preform in FIGS. 2A, 2B and 2C indicate the direction of the material flow (in the plane of the paper) during the compression process. Three stages, FIG. 2A, FIG. 2B and FIG. 2C are shown. The lines in the preform in FIG. 2A, 2B and 2C indicate the direction of the material flow (in the plane of the paper) during the compression process.

FIG. 3 is a schematic diagram like that of FIG. 2, with a polymer preform (FIG. 3A) comprised of three layers of the same polymer, again at a plurality of different stages of the process (FIGS. 3B and 3C). Again, three stages, A, B, and C are shown, and the final product is shown at FIG. 3D. The lines in the preform in FIGS. 3A, 3B and 3C indicate the direction of the material flow (in the plane of the paper) during the compression process.

FIG. 4 is a schematic diagram of a similar mold with an UHMWPE preform between the mold plates (FIG. 4A) as it is being deformed (FIGS. 4B, 4C, and 4D) into an acetabular liner (FIG. 4E), and shows it at a plurality of different stages of the process. The liner is the preform in FIGS. 4A—4E. The lines in the preform 13 indicate the direction of the material flow (in the plane of the paper) during the compression process.

FIG. 5 is a similar diagram of a modification of the schematic view of the mold in FIG. 4, in which one part of the mold cavity can be moved relative to the rest for controlling the deformation in the product topologically. Steps 5A, 5B, 5C and 5D are shown as well as the final product of 5E. The lines in the preform of FIGS. 5A–5E indicate the direction of the material flow (in the plane of the paper) during the compression process.

FIG. 6 is a similar diagram of a schematic modification of the preform in FIG. 3 which is comprised of two layers of UHMWPE and a layer of woven or knitted reinforcing fibers is shown as FIG. 6A; and molding stages 6B and 6C are shown as well as the final product of FIG. 6D. The lines in the preform in FIGS. 6A–6D indicate the direction of the material flow (in the plane of the paper) during the compression process.

FIG. 7 is a reproduction of a photograph of an acetabular liner as prepared by this invention.

FIG. 8 is a schematic diagram of a mold with an UHMWPE preform between the mold plates as FIG. 8A and at a stage (FIG. 8B as it is being deformed into a tibial plate; and as a final product FIG. 8C). The lines in the preform in FIGS. 8A, 8B and 8C indicate the direction of the material flow (in the plane of the paper) during the compression process.

FIG. 9 is a reproduction of a photograph of a tibial plate as prepared by this invention.

FIG. 10 is a graph, showing tensile stress, versus % elongation behavior of an UHMWPE prepared by (a) this invention and (b) conventional compression molding.

FIG. 11 is a view similar to FIG. 1 in which the perimeter zone is in the form of a reservoir.

DESCRIPTION OF SOME PREFERRED EMBODIMENTS

According to the invention, solid-state deformed products with enhanced and balanced mechanical properties can be made with high-molecular-weight polymers such as ultra-high-molecular-weight polyethylene by: first, preparing the UHMWPE preform and, subsequently, processing it, using an open-mold configuration 10 of FIG. 1. The mold 10 may be circular, rectangular, or of any other shape.

There is an upper mold plate 11 a lower mold plate 12, and a polymer preform 13. The UHMWPE can be obtained from ram-extruded or compression-molded stock. U.S Pat. No. 4,587,163 discloses that the use of a high temperature, i.e., above 220° C., results in a homogeneous melt-crystallized morphology in comparison with a meltcrystallized morphology prepared below 220° C. A UHMWPE preform 13 prepared at above 220° C. under, e.g., a pressure of 15,000 psi has better mechanical properties and, upon its solid-state deformation using the methodology of this invention, exhibits better optical properties than a preform prepared at less than 220° C. and therefore not having the complete fusion of the UHMWPE.

The processing methodology of this invention comprises the following two steps: a) the thermal condition of the preform and b) its solid-state deformation.

The UHMWPE preform 13 can be heated, prior to its use for the deformation step, outside the mold or in the mold to 80°–130° C. and preferably between 120° C. and 130° C.

The mold in FIG. 1 comprising the mold cavity 16 and the perimeter zone 17 can be heated to a temperature range of 100°–180° C. and preferably between 120° C. and 165° C. The particular mold temperature setting may not coincide with the temperature of the preform prior to its deformation. A suitable choice of temperatures can be made in consideration of the deformation cycle, which can be as short as several minutes and the compression-load conditions.

After heating the polymer preform 13 and the mold 10 to some particular temperatures, the polymer preform 13 is compressed between the mold plates 11 and 12 in FIG. 2A so that it is deformed in the solid state between the plates 11 and 12 to or beyond the mold boundaries 14 and 15 in FIG. 2B to form a perimeter polymer mass 18 in FIG. 2B. The deformation takes place under a gradually increasing compression until the maximum pressure is reached. After the maximum pressure is reached, the mold 10 in FIG. 2 is cooled to ambient temperature; the cooling time can be as short as a few minutes, if rapid cooling is preferred. After cooling to ambient temperature, the product shown in FIG. 2D comprising the final shaped product 19 with the enhanced properties and the perimeter polymer mass 18 is removed. The final product 19 in FIG. 2D can be separated from the perimeter mass 18 by stamping or other process after its removal from the mold 10, or after thermal (annealing) or post-processing conditions, e.g., radiation cross-linking.

Unlike the prior-art solid-state-forming processes, which involve the solid-state deformation of the polymer to an extent (deformation ratio) which is determined by the relative dimensions of the preform and the mold cavity, in the process of the invention the deformation ratio is controlled by the material properties of the polymer under the employed temperature and pressure conditions during the deformation process. A balance of the deformation ratio in different directions can be attained by adjusting the shape of the preform relative to the shape of the mold cavity, by adjusting the gap and the shape of the perimeter zone in different locations and by moving selected components of the mold cavity (FIG. 5).

FIG. 2 shows the deformation of the preform 13 during its compression into the final product 19. The shaded portion in FIG. 2D shows the removed perimeter polymer 18. At FIG. 2A the mold 10 with its upper plate 11 and its lower plate 12 are shown, along with polymer preform 13. The lines in the deforming preform 13 indicate the direction of the material flow (in the plane of the paper) during the compression process.

FIG. 2 shows the polymer preform 13 at different stages of its deformation under compression in the mold. The preform in the mold at the beginning of the deformation is shown in FIG. 2A, at an intermediate stage in 2B and at the end of the deformation in 2C. The final product 19 is shown at 2D. The shaded portion in 2D shows the removed perimeter polymer component 18. In FIG. 2 at A the polymer preform 13 is placed in the mold 10 and the mold 10 is still under no compression. At 2B the plates 11 and 12 are compressed towards each other, compressing the polymer preform 13 and resulting in its deformation. The deformed preform is comprised of a portion 19 in the mold cavity 16 and a perimeter polymer component 18 which accumulates in the perimeter zone 17 of the mold beyond the mold boundaries 14 and 15. At 2C there is further compression, and where the so produced polymer configuration is removed from the mold 10 after its cooling to ambient temperature and is separated from its perimeter polymer component 18, it becomes the final product 19 shown in 2D.

FIG. 3 shows the polymer preform 13 comprised of three layers 13A, 13B, and 13C of the same UHMWPE resin at different stages of its deformation. Under compression in the mold, the preform 13 in the mold 10 at the beginning of the deformation is shown in 3A, at an intermediate stage in 3B, and at the end of the deformation in 3C. The final three-layer product 19A is shown in 3D; the shaded portion in D shows the removed perimeter polymer component 18A.

In FIG. 3A the polymer preform 13 comprised of the three layers 13A, 13B and 13C of UHMWPE is placed in the mold 10, and the mold 10 is still under no compression. At FIG. 3B, the plates 11 and 12 are compressed toward each other as described above, compressing the polymer preform 13 and resulting in its deformation. At 3C there is further compression, as explained above and in the examples, to give a polymer configuration comprised of a laminate product 19A in the mold cavity 16 and a perimeter polymer component 18A in the perimeter zone 17 of the mold which, when removed from the mold 10 after its cooling to ambient temperature and separation from its perimeter polymer component 18A, it becomes a final product 19A shown in 3D. A larger number of layers can be deformed simultaneously in this arrangement. Also, the middle layer(s) can be fiber filled, whereas the outside layers can be unfilled.

FIG. 4 shows the deformation of ultra-high-molecular-weight polyethylene preform 13 into an acetabular liner or a product 19 that at least looks like an acetabular liner. Again, the sheet-like portion in 4D shows the removed perimeter polymer 28.

In FIG. 4A an open mold 20 with an upper mold member 21 and a lower mold member 22 is shown with a polymer preform 13 between them. The dotted lines indicate the boundaries of the mold cavity 26 from the perimeter zone 27. At 4B the upper plate 21 compresses the preform 13, so that part of it flows down into a cavity 26 at FIG. 4B within the lower member 22. At 4C the compression continues and at 4D a product comprised of portions 29 and 28 is shown which when is removed from the mold 10 after its cooling to ambient temperature and separated from its perimeter component 28, it results in the final acetabular liner 29 in FIG. 4E.

FIG. 5 shows the deformation of ultra-high-molecular-weight polyethylene preform 13 into an acetabular liner 39 or a product that at least looks like an acetabular liner under conditions which involve the particular displacement of a plunger member 30 (see 5A, 5B and 5C) of a top plate 31 to accomplish the compression deformation of the preform first in a mold cavity 36 of a lower plate 32 and then the displacement of the top plate member 31 to accomplish the compression deformation of a the perimeter polymer 38. The so-produced product comprised of portion 39 and 38 shown in 5D, when removed from the mold after its cooling to ambient temperature and separated from the component (38), it results in the final product 39 shown in 5E.

FIG. 6 shows the polymer preform 43 comprised of three layers 43A, 43B, and 43C of the same UHMWPE resin at different stages of its deformation under compression in the mold. The two outside layers 43A and 43C of the layered polymer preform are of semicrystallized UHMWPE and the middle layer 43B of woven or knitted UHMWPE high modulus and strength fibers. The preform 43 in the mold at the beginning of the deformation is shown in 6A, at an intermediate stage in 6B and at the end of the deformation in 6C. The final fiber reinforced laminate product 49 of UHMWPE with UHMWPE fibers is shown in 6D.

In FIG. 6A the polymer preform 43 is placed in the mold and the mold is still under no compression. At 6B the plates 11 and 12 are compressed toward each other as described above, compressing the polymer composite preform and resulting in its deformation. At 6C there is further deformation as explained above to give a polymer configuration comprised of a laminate component 49 in the mold cavity and a perimeter polymer component 48 in the perimeter zone of the mold which when removed from the mold after its cooling to ambient temperature and separation from its perimeter polymer component 48, it becomes a final fiber reinforced laminate product 49 shown in 6D. During the compression steps from 6A to 6C, the reinforcing fiber layer 43B is kept under tension.

FIG. 7 is a photograph of an acetabular liner 50 as prepared by this invention, which, besides its enhanced mechanical properties, it also fairly transparent. In comparison, a product produced by conventional molding or machining in opaque.

FIG. 8 shows a schematic diagram of a mold 60 with an UHMWPE preform 63 of 8A as is being deformed in 8B into a tibial-like plate product 69 between mold plates 61 and 62. After separating the plate product 69 from its perimeter polymer 68, it becomes the tibial plate 69 shown in 8C.

FIG. 9 is a photograph of a tibial plate 69 as prepared by this invention. Again, the product 69 of this invention is transparent in comparison to the conventionally produced products.

FIG. 10 is a graph that shows the stress versus & elongation behavior of an UHMWPE prepared by (a) this invention and (b) conventional compression molding.

FIG. 11 is a schematic view of a modified form of mold having a reservoir separated from the mold cavity by a flow-through region.

EXAMPLE 1

In one experiment, an UHMWPE, and UHMWPE cylindrical preform 13 (diameter 3 inches) prepared according to the methodology of U.S. Pat. No. 4,587,163, by heating a powder stock (Hostalen 412 GUR, weight average molecular weight greater than 3 million) to 300° C. and then cooling to 140°-150° C. and compressing it under 15,000 psi and then cooling it further to ambient temperature, was heated by air convection in an oven to 90° C. (the temperature was measured by a thermocouple inside a reference preform of the same dimensions), and was placed in the mold 10 of FIG. which was preheated to 130° C. Then, the preform 13 was compressed under a pressure of 100 MPa into a disc-like product of deformation ratio approximately 3, as determined from the displacement of marks, in the mold cavity 16 and a perimeter polymer 18 in the perimeter zone 17 as shown in FIG. 2B and 2C. After the maximum pressure is reached, the mold is cooled to ambient, and the final product 19 with the attached perimeter polymer mass 18 is removed from the mold 10 and separated from the polymer mass 18 by machining. Upon removal from the mold and separation from the perimeter polymer mass, the product 19 "shrinks" by springback by only ~8%. The product (3 mm thick) is transparent and free from unfused powder particles and has a Young's modulus of 1.3 GPa and a tensile strength of 126 MPa at 42% elongation.

EXAMPLE 2

In another independent experiment, an UHMWPE cylindrical preform 13 (diameter 3 inches) prepared from conventionally compression molded stock of the same UHMWPE resin as with Example 1, was heated to 90° C. and was placed in the mold 10 (FIG. 2) preheated to 130° C. and compressed into a disc-like product 19 of deformation ratio approximately 3 under a pressure of 100 MPa. After cooling the mold 10 to ambient temperature, the product 19 with the attached perimeter polymer mass 18 was removed from the mold and separated from the polymer mass by stamping. Upon removal from the mold 10 and separation from the perimeter polymer mass 18, the product 19 "shrunk" by ~10%. The product 19 (3 mm thick) was transparent but with unfused powder particles dispersed throughout the product; its Young's modulus was 1 GPa, and its tensile strength 91.5 MPa at 104% elongation.

EXAMPLE 3

The same procedure as with Example 1 was used, with the modification that the final product 19 was separated from the perimeter polymer mass 18 three days after being processed. The product shrank by 1.6%.

EXAMPLE 4

The same procedure as with Example 2 was used, with the modification that the preform 13 was heated to 80° C., the mold temperature was 128° C., and the compression was 75 MPa. The product 19, after its removal from the perimeter polymer mass 18, shrank by 3%; its deformation ratio was 2, its Young's modulus was 0.8 GPa, and its tensile strength was 81 MPa at 90% elongation.

EXAMPLE 5

The same procedure as with Example 1 was used, with the modification that a UHMWPE preform portion 13A (a Hostalen 412 GUR) was "sandwiched" between two thin layers 13B and 13C (2 mm thick) of UHMWPE of the same polymer resin before it was placed in the mold 10 in FIG. 3. The preform components were heated to 95° C., the mold temperature was 130° C. and the compression was 200 MPa. The final product laminar 19A in FIG. 3D was transparent. An evaluation of the mechanical properties of one of the deformed thin layers (13B or 13C in FIG. 3C) after its separation from the final product 19A in FIG. 3D showed that the Young's modulus was 1.2 GPa and the tensile strength 92 MPa at 58% elongation.

EXAMPLE 6

In another independent experiment, an UHMWPE preform 13 (Hostalen 412 GUR) prepared according to the methodology of U.S. Pat. No. 4,587,163, and described in Example 1, was heated to 100° C. and after it was placed in the mold 20 (FIG. 4) which was preheated to 155° C. was compressed under 275 MPa into an acetabular shell or liner product 29 in 4D, which was separated from its perimeter polymer mass 28 after cooling the mold 20 to ambient temperature. The acetabular shell or liner 29 in 4E shrunk by approximately 1.5%. The deformation ratio of the hemispherical section of the acetabular product 29 in the mold cavity 26 was uniform and was determined from the displacement of marks on its outer surface to be 2.3. As shown in FIG. 7, the product 50 was fairly transparent. Tensile specimens prepared from ribbons cut along the perimeter of the hemispherical portion of the product 29 exhibited a tensile strength of 60 MPa at a 72% elongation.

EXAMPLE 7

In another independent experiment, an UHMWPE preform 13 prepared from commercially available compression molded stock (Hostalen GUR 412) was heated to 100° C. and it was placed in the mold 20 shown in FIG. 4, which was preheated to 155° C.; then it was processed under conventional compression molding conditions under 10 MPa i.e., in a closed mold configuration, into an acetabular cup product 29. This product, when retrieved from the mold, had shrunk by 12% and was opaque. Tensile specimens prepared from ribbons cut along the perimeter of the hemispherical portion of this acetabular product exhibited a tensile strength of 35 MPa at a 318% elongation. According to prior literature the maximum tensile strength of compression molded UHMWPE is about 40 MPa.

EXAMPLE 8

In another independent experiment, one layer 43B in FIG. 6 of woven UHMWPE high modulus fibers (Allied Spectra fibers) held under tension 21 was placed between two layers 43A and 43C of UHMWPE (Hostalen 412 GUR) (each 10 mm thick), which were preheated to 120° C.; this assembly was used as a preform which was placed in the mold shown in FIG. 6, which was preheated to 130° C. and compressed under 120 MPa to produce an UHMWPE laminar product 49, which was separated from its perimeter polymer mass 48 after cooling the mold 10 to ambient temperature. The so-produced product 49 in 6D was comprised of a solid-state deformed matrix of UHMWPE (two layers) 43A and 43C reinforced with UHMWPE fibers 13C.

EXAMPLE 9

The same procedure as with Example 8 was used, with the modification that the preform 43 in FIG. 6 was placed in the mold 20 shown in FIG. 4 to produce an UHMWPE laminar acetabular shell or liner 29 comprised of two solid-state deformed layers of UHMWPE reinforced with a layer of UHMWPE fibers in between.

EXAMPLE 10

In another independent experiment, an UHMWPE (Hostalen 412 GUR) square preform (1.5 in.×1.5 in.), which was prepared according to the methodology of the U.S. Pat. No. 4,587,163 discussed in Example 1, was heated to 100° C. and was placed in the mold 60 shown in FIG. 8, which was preheated to 130° C. and was compressed into a tibial-plate-like product 69 shown in 8B under a pressure of 140 MPa After the mold 60 was cooled to ambient temperature, the product 69 was removed from the mold, and the tibial plate 69 was separated from its perimeter polymer mass 68 shown in FIG. 8C. The so-produced tibial plate 69 was transparent, in contrast to the currently produced products which are opaque. A photograph is shown in FIG. 9. Because of the geometrical complexity of the tibial plate 69 (e.g., its thickness varied from approximately 0.25 in to 0.6 in. in different parts of the plate), the evaluation of its mechanical properties was made with tensile samples which were cut off and machined from its back plate side, which was flat The Young's modulus was 1.2 Gpa, and the tensile strength was 87 MPa at 97.5% elongation.

EXAMPLE 11

The same procedure was used as with Example 10, with the provision that the mold pressure was 250 MPa. The thickness variation range of the tibial plate was reduced to approximately 0.12-0.47 in. The Young's modulus was 1.2 GPa, and the tensile strength was 90.7 MPa at 103% elongation. In other words, the thickness of the tibial plate could be reduced without sacrificing its mechanical properties.

In addition to the biomedical uses suggested in this patent application, there are numerous other applications which include impact resistant structures, ballistic applications, structural components combining wear resistance and improved creep, fatigue, and in general load bearing capacity. These points become apparent when one considered the stress —% elongation behavior of an UHMWPE with isotropic mechanical properties as produced by this patent and the conventionally molded UHMWPE in FIG. 10.

The UHMWPE of this application shows a small elastic hysterisis (i.e. the energy dissipated as heat in one cycle of dynamic test), has a significantly higher deformation energy (i.e. energy to deform the material by a specified amount e.g., to a 10% strain at which the conventionally produced UHMWPE deforms plastically), it has a much higher bearing strength (i.e. the maximum usable stress that can be developed by the material at a particular strain) and a significantly higher bulk modulus of elasticity (which relates proportionally to the Young's modulus), and it has a higher resistance to cold flow and hence to creep; preliminary results show also that it has an impact resistance at least 2× higher from the conventionally molded UHMWPE.

To those skilled in the art to which this invention relates, many changes in construction and widely differing embodiments and applications of the invention will suggest themselves without departing from the spirit and scope of the invention. Such embodiments may include the solid-state deformation of the UHMWPE in a mold in which the perimeter zone is in the form of a reservoir instead of an "open" space around the mold cavity. This is shown in the schematic view of FIG. 11, depicting the polymer deformed in the mold, in which the perimeter zone 17A is a reservoir separated by a mold cavity 16 by a "flow through" region 17B. The flow through region 17B allows excess polymer in mold cavity 16 to flow beyond the mold boundaries 14 and 15 for the purpose of attaining a particular deformation ratio in the mold cavity 16, and to accumulate into or fill the perimeter zone 17A. The solid-state-deformed product in the mold cavity 16 can be separated from its perimeter components generated in the flow through region 17B and the perimeter zone 17A substantially as described previously. Also, the so-produced solid-state deformed UHMWPE can be used as a precursor for its machining into a final product benefiting from the enhanced properties of the solid state deformed UHMWPE.

What is claimed is:

1. A method for producing an UHMWPE product with enhanced planar mechanical properties comprising:

solid-state deforming an initial UHMWPE semicrystalline morphologoy under compression in a mold comprising a mold cavity and a perimeter zone including:

orienting a polymer preform having a volume greater than said mold cavity, thereby providing an excess amount of the polymer and extending it in more than one direction in the mold cavity and the perimeter zone to an extent which is limited by the material properties of the polymer under the employed processing conditions, which include the temperature of the initial UHMWPE semicrystalline morphology, the mold temperature, the compression load and the geometrical configuration of the mold cavity and the perimeter zone, deforming the excess amount of polymer past the boundaries of the mold cavity into a perimeter zone surrounding the mold cavity for the purpose of controlling the deformation of the polymer product in the mold cavity, cooling the oriented and extended UHMWPE under compression to ambient temperature for maintaining the maximum orientation and extension attained during the said solid-state deformation process, separating the polymer product in the mold cavity from the product in the perimeter zone of the mold cavity, said solid-state deformation process taking plass at a mold temperature and compression conditions to obtain an UHMWPE product having a markedly transformed morphology, as compared with the said initial UHMWPE morphology, said product comprising oriented and extended molecular chains in more than one direction and exhibiting mechanical properties in more than one direction, that are higher than those of the initial UHMWPE morphology prior to its deformation, the magnitude depending on the extend of deformation.

2. The method of claim 1 wherein the mold cavity is not enclosed.

3. The method of claim 1 wherein the perimeter zone has a reservoir enabling the UHMWPE to flow into it.

4. The method of claim 1 in which the said solid-state deformation process takes place at a mold temperature and compression condition to obtain an equibiaxially oriented and extended UHMWPE product with enhanced isotropic properties.

5. The method of claim 1 in which the said solid-state deformation process takes place at a mold temperature and compression condition to obtain a biaxially and extended UHMWPE with balanced properties in more than one direction.

6. The method of claim 1 in which the initial UHMWPE semicrystalline morphology is in the form of a melt crystallized preform.

7. The method of claim 1 in which the initial UHMWPE semicrystalline morphology is in the form of a sintered powder preform.

8. The method of claim 1 in which the excess amount of the deformed polymer past the boundaries of the mold cavity in the perimeter zone surrounding the mold cavity acts as a self generating tenter frame by holding the deformed polymer in the mold cavity under tension after its removal from the mold.

9. The method of claim 1 in which the said solid-state deformation process takes place with the UHMWPE preform heated prior to its deformation in the temperature range of 80°–120° C. at a mold temperature in the temperature range of 120°–180° C. and under a compression of at least 20 MPa.

10. The method of claim 1 in which the semicrystalline preform is made of a plurality of UHMWPE laminar layers which can be solid-state deformed simultaneously into one laminar product.

11. The method of claim 10 in which at least one of the UHMWPE layers of the semicrystalline preforms is comprised of reinforcing high modulus fibers.

12. The method of claim 11 in which reinforcing high modulus fiber layers are comprised of uniaxially oriented fibers, each said reinforcing layer being separated by a non-reinforcing layer and with its fibers in a different direction from the fibers in adjacent reinforcing layers.

13. The method of claim 11 in which the layer of fiber reinforcement is in the form of woven fibers.

14. The method of claim 11 in which the reinforcing fibers are ultra-high-molecular-weight polyethylene.

15. The method of claim 1 in which said UHMWPE product is an orthopaedic prosthetic implant.

16. The method of claim 15 in which the orthopaedic product is an acetabular shell.

17. The method of claim 15 in which the orthopaedic product is an acetabular liner.

18. The method of claim 15 in which the orthopaedic product is a tibial plate.

* * * * *